United States Patent
Shimoyama

(10) Patent No.: US 12,350,096 B2
(45) Date of Patent: Jul. 8, 2025

(54) ULTRASONIC ENDOSCOPE

(71) Applicant: FUJIFILM Corporation, Tokyo (JP)

(72) Inventor: Yuto Shimoyama, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 176 days.

(21) Appl. No.: 18/184,258

(22) Filed: Mar. 15, 2023

(65) Prior Publication Data

US 2023/0309953 A1 Oct. 5, 2023

(30) Foreign Application Priority Data

Mar. 29, 2022 (JP) ................................ 2022-053645

(51) Int. Cl.
*A61B 8/12* (2006.01)
*A61B 8/00* (2006.01)

(52) U.S. Cl.
CPC .............. *A61B 8/12* (2013.01); *A61B 8/4494* (2013.01)

(58) Field of Classification Search
CPC .. A61B 8/12; A61B 8/56; A61B 8/445; A61B 8/4483; A61B 8/4494; H05K 1/02; H05K 2201/05
See application file for complete search history.

(56) References Cited

U.S. PATENT DOCUMENTS

2013/0072801 A1* 3/2013 Hiraoka ............... G10K 11/004
                                                             600/463
2020/0205777 A1* 7/2020 Kumata ................... A61B 8/12

FOREIGN PATENT DOCUMENTS

JP       11-276489 A    10/1999
JP    2001-314405 A    11/2001
JP    2002-153467 A     5/2002

* cited by examiner

*Primary Examiner* — Boniface N Nganga
(74) *Attorney, Agent, or Firm* — Birch, Stewart, Kolasch & Birch, LLP

(57) ABSTRACT

An ultrasonic endoscope includes an ultrasound transducer, a distal end body block component in which an observation optical system and an illumination optical system are mounted, a channel block component, and a flexible printed circuit part that is disposed inside the distal end body block component and is connected to the ultrasound transducer, the flexible printed circuit part includes a transducer connection portion, an offset wiring portion that is positioned on an opposite side to the transducer connection portion and is disposed in an offset manner at a position away from a longitudinal axis toward an outside in a radial direction of the longitudinal axis with respect to the transducer connection portion, and an intermediate connection portion that connects the transducer connection portion and the offset wiring portion, the offset wiring portion has a cable bonding portion to which loose cables are bonded, and the cable bonding portion is covered with an insulating member that is positioned inside the distal end body block component.

13 Claims, 11 Drawing Sheets

FIG. 6
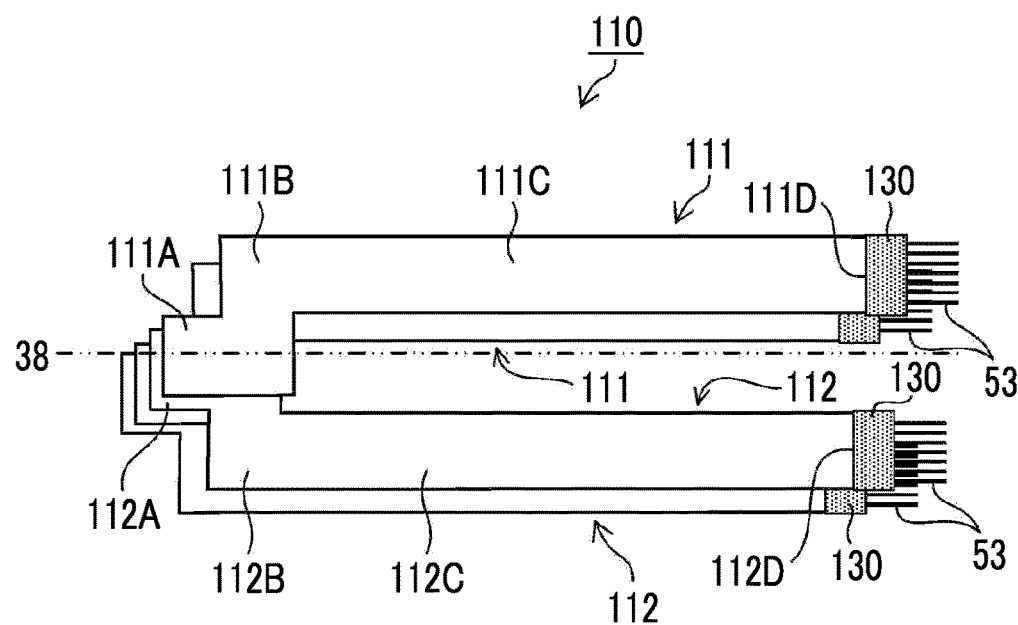
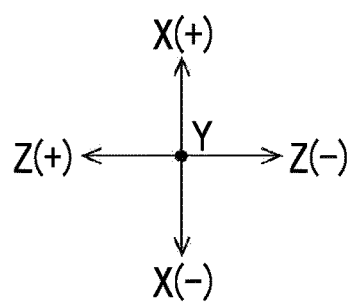

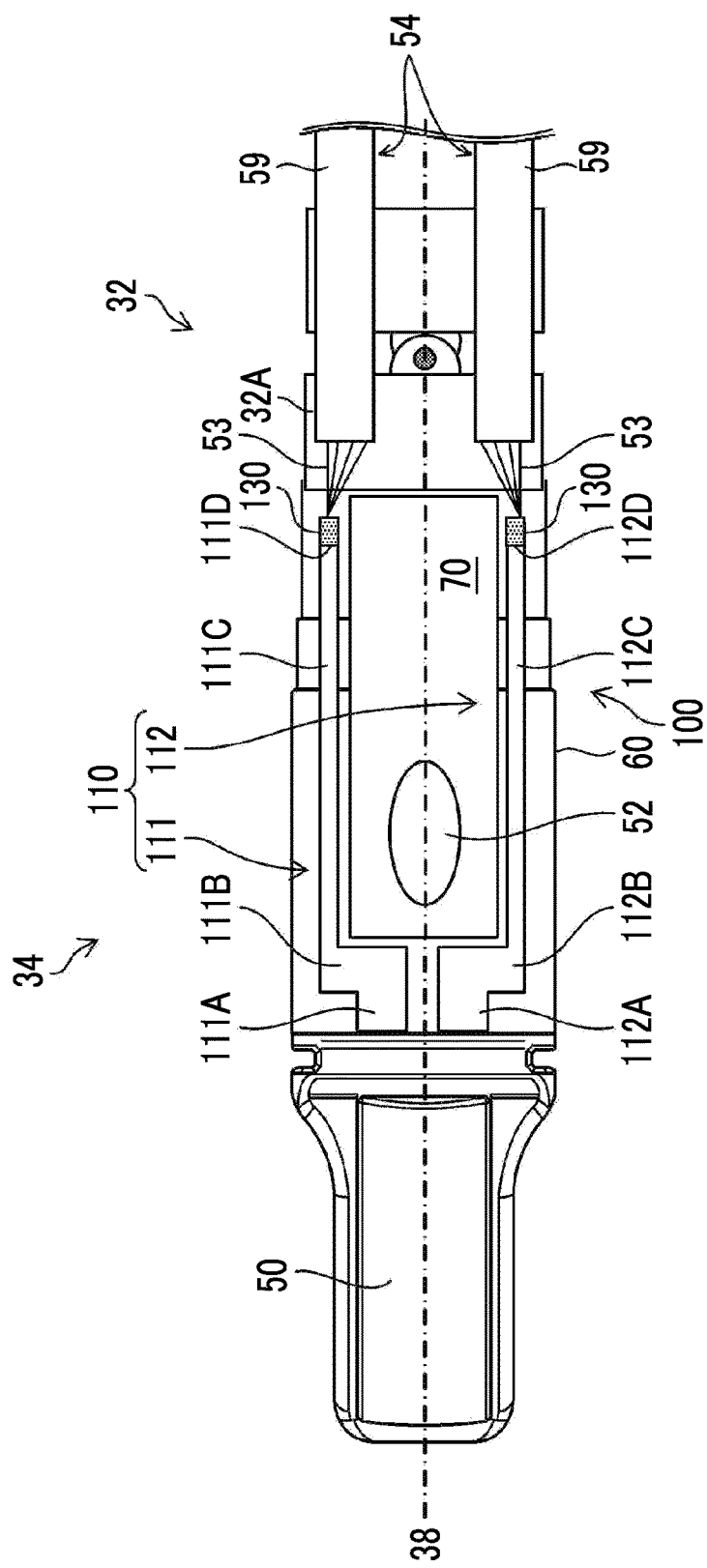
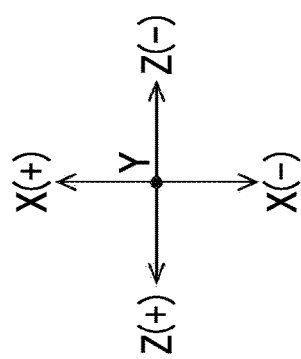
FIG. 7

FIG. 10
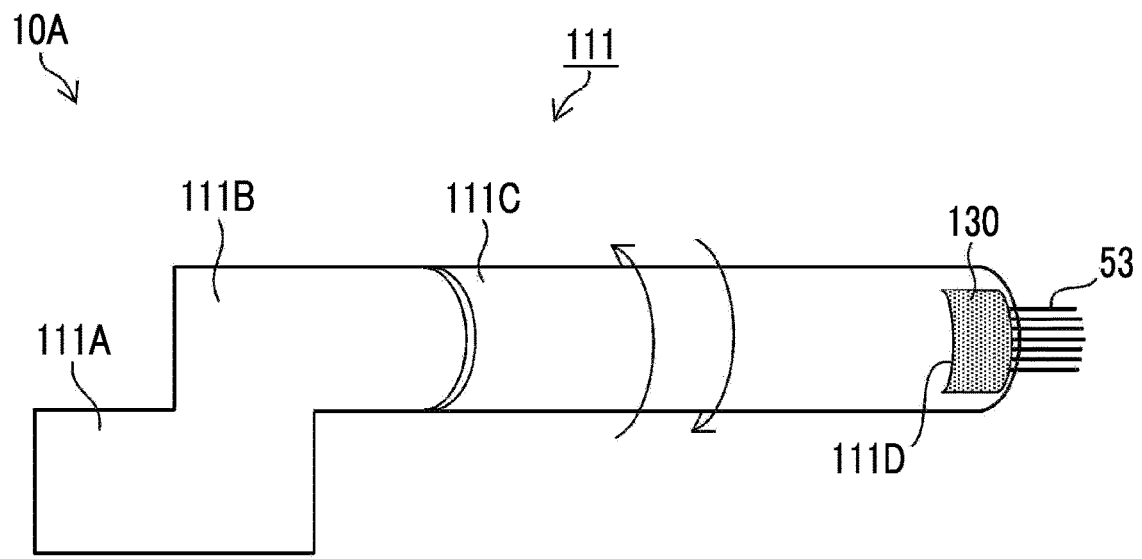
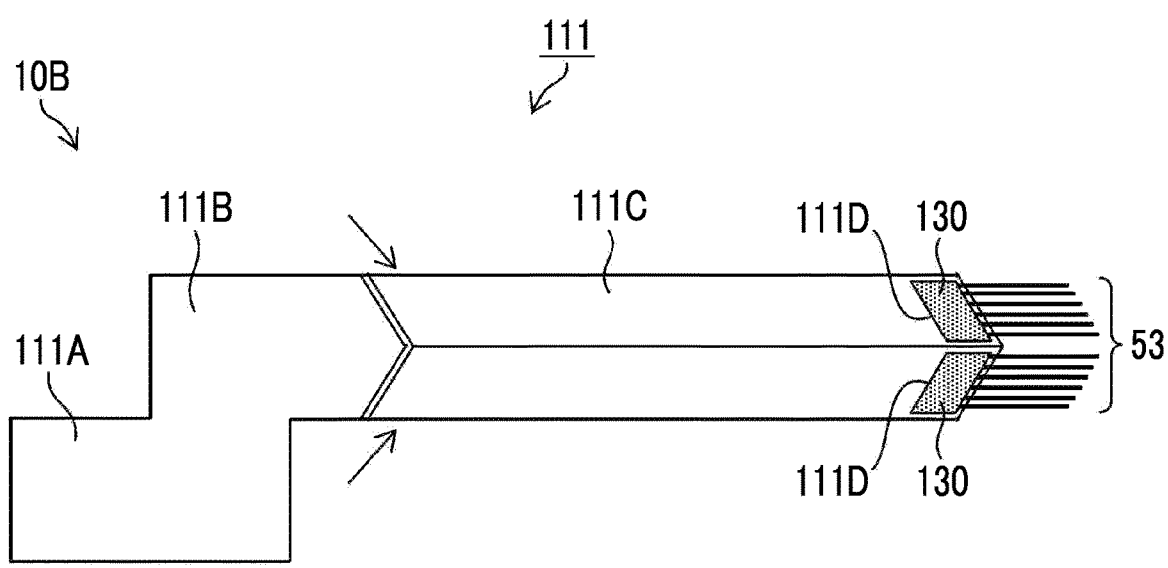

ULTRASONIC ENDOSCOPE

CROSS-REFERENCE TO RELATED APPLICATION

The present application claims priority under 35 U.S.C § 119(a) to Japanese Patent Application No. 2022-053645 filed on Mar. 29, 2022, which is hereby expressly incorporated by reference, in its entirety, into the present application.

BACKGROUND OF THE INVENTION

1. Field of the Invention

The present invention relates to an ultrasonic endoscope.

2. Description of the Related Art

As an ultrasonic endoscope, an ultrasonic endoscope that comprises an electronic scanning type ultrasound oscillator in a distal end part of an insertion part of an endoscope is known. Then, the ultrasonic endoscope punctures a treatment tool, such as a puncture needle, led out from an outlet port of the distal end part through a treatment tool insertion channel into a lesion part to collect a cell tissue of a lesion part while acquiring an ultrasound image of the lesion part using the ultrasound oscillator.

The ultrasonic endoscope comprises an observation optical system and an illumination optical system in addition to the ultrasound oscillator, and can also perform observation by an optical image, whereby it is possible to reliably guide the puncture needle to a target site through the observation by the optical image until the puncture needle is made to approach and is punctured into a body wall.

In such an ultrasonic endoscope, a technique that electrically connects a cable of a signal line and an ultrasound transducer through a flexible printed circuit is known (JP2002-153467A, JP1999-276489A (JP-H11-276489A), and JP2001-314405A).

SUMMARY OF THE INVENTION

The ultrasonic endoscope is required to secure the insulation performance of the distal end part as ultrasound safety standards. On the other hand, the ultrasonic endoscope is required to have improved manufacturing suitability.

In an ultrasonic endoscope described in JP2002-153467A, since loose cables and a flexible printed circuit are bonded in a bendable part, the cables and the flexible printed circuit may be disconnected due to a bending operation, and insulation performance may not be secured.

In an ultrasonic endoscope described in JP1999-276489A (JP-H11-276489A), a flexible printed circuit and loose cables are connected just near a proximal end side of an ultrasound transducer. For this reason, styling of the loose cables is needed in a distal end part. In a case where the distal end part has a small diameter, since it is difficult to insert the cables into the distal end part, it is not easy to provide improved manufacturing suitability.

In an ultrasonic endoscope described in JP2001-314405A, like the ultrasonic endoscope described in JP2002-153467A, since loose cables and a flexible printed circuit are bonded in a bendable part, the cables and the flexible printed circuit may be disconnected due to a bending operation, and insulation performance may not be secured.

The present invention has been accomplished in view of such a situation, and an object of the present invention is to provide an ultrasonic endoscope that facilitates insertion processing in a distal end part and can secure insulation performance.

According to a first aspect, there is provided an ultrasonic endoscope comprising an ultrasound transducer in a distal end part, a distal end body block component in which the ultrasound transducer, an observation optical system, and an illumination optical system are mounted, a channel block component that is a component to be assembled inside the distal end body block component and in which a channel into which a treatment tool is inserted is mounted, and a flexible printed circuit part that is disposed inside the distal end body block component and is connected to the ultrasound transducer, in which the flexible printed circuit part includes a transducer connection portion that is positioned on one side to be an ultrasound transducer side, an offset wiring portion that is positioned on the other side to be an opposite side to the one side, is disposed in an offset manner at a position away from a longitudinal axis toward an outside in a radial direction of the longitudinal axis with respect to the transducer connection portion, and is formed along the channel block component, and an intermediate connection portion that connects the transducer connection portion and the offset wiring portion, the offset wiring portion has a cable bonding portion to which loose cables are bonded, on an opposite side to the intermediate connection portion, the cable bonding portion is covered with an insulating member, and the insulating member is positioned inside the distal end body block component.

According to a second aspect, in the ultrasonic endoscope, the flexible printed circuit part has a first offset wiring portion and a second offset wiring portion disposed in an offset manner in opposite directions to each other from the longitudinal axis, as the offset wiring portion, and the channel block component is disposed between the first offset wiring portion and the second offset wiring portion.

According to a third aspect, in the ultrasonic endoscope, the flexible printed circuit part has a first intermediate connection portion and a second intermediate connection portion extending in opposite directions to each other from the transducer connection portion toward the outside in the radial direction, as the intermediate connection portion, the first intermediate connection portion and the first offset wiring portion are connected, and the second intermediate connection portion and the second offset wiring portion are connected.

According to a fourth aspect, in the ultrasonic endoscope, the flexible printed circuit part has a first transducer connection portion and a second transducer connection portion disposed separately from each other, as the transducer connection portion, the first transducer connection portion and the first intermediate connection portion are connected, and the second transducer connection portion and the second intermediate connection portion are connected.

According to a fifth aspect, in the ultrasonic endoscope, the flexible printed circuit part has a first flexible printed circuit and a second flexible printed circuit disposed separately from each other.

According to a sixth aspect, in the ultrasonic endoscope, a plurality of the flexible printed circuit parts are disposed to overlap in a thickness direction of the flexible printed circuit part.

According to a seventh aspect, in the ultrasonic endoscope, a plane direction of the offset wiring portion is the same direction as a plane direction of the transducer connection portion.

According to an eighth aspect, in the ultrasonic endoscope, the flexible printed circuit part is bent or torsionally deformed along a straight line parallel to the longitudinal axis, and the plane direction of the offset wiring portion is a direction perpendicular to a plane direction of the transducer connection portion.

According to a ninth aspect, in the ultrasonic endoscope, the channel block component has an opening forming surface in which an outlet port of the treatment tool is formed, and a plane direction of the offset wiring portion is a direction perpendicular to a plane direction of the opening forming surface.

According to a tenth aspect, in the ultrasonic endoscope, the flexible printed circuit part is disposed inside the distal end body block component in a state in which a shape of at least a part of the flexible printed circuit part is a cylindrical shape or a tubular shape.

According to an eleventh aspect, in the ultrasonic endoscope, the distal end body block component has an ultrasound block component in which the ultrasound transducer is mounted, and an optical system block component in which the observation optical system and the illumination optical system are mounted.

According to a twelfth aspect, in the ultrasonic endoscope, a forming material of the distal end body block component includes resin and metal, and a forming material of the channel block component is metal.

According to the present invention, insertion processing in a distal end part is facilitated, and insulation performance can be secured.

BRIEF DESCRIPTION OF THE DRAWINGS

FIG. 6 is a diagram illustrating a second modification example.
FIG. 7 is a diagram illustrating a third modification example.
FIG. 10 is a diagram illustrating a sixth modification example.

DESCRIPTION OF THE PREFERRED EMBODIMENTS

Hereinafter, an ultrasonic endoscope according to the present invention will be described referring to the accompanying drawings.

Overall Configuration of Ultrasonic Endoscope

Figure 1:
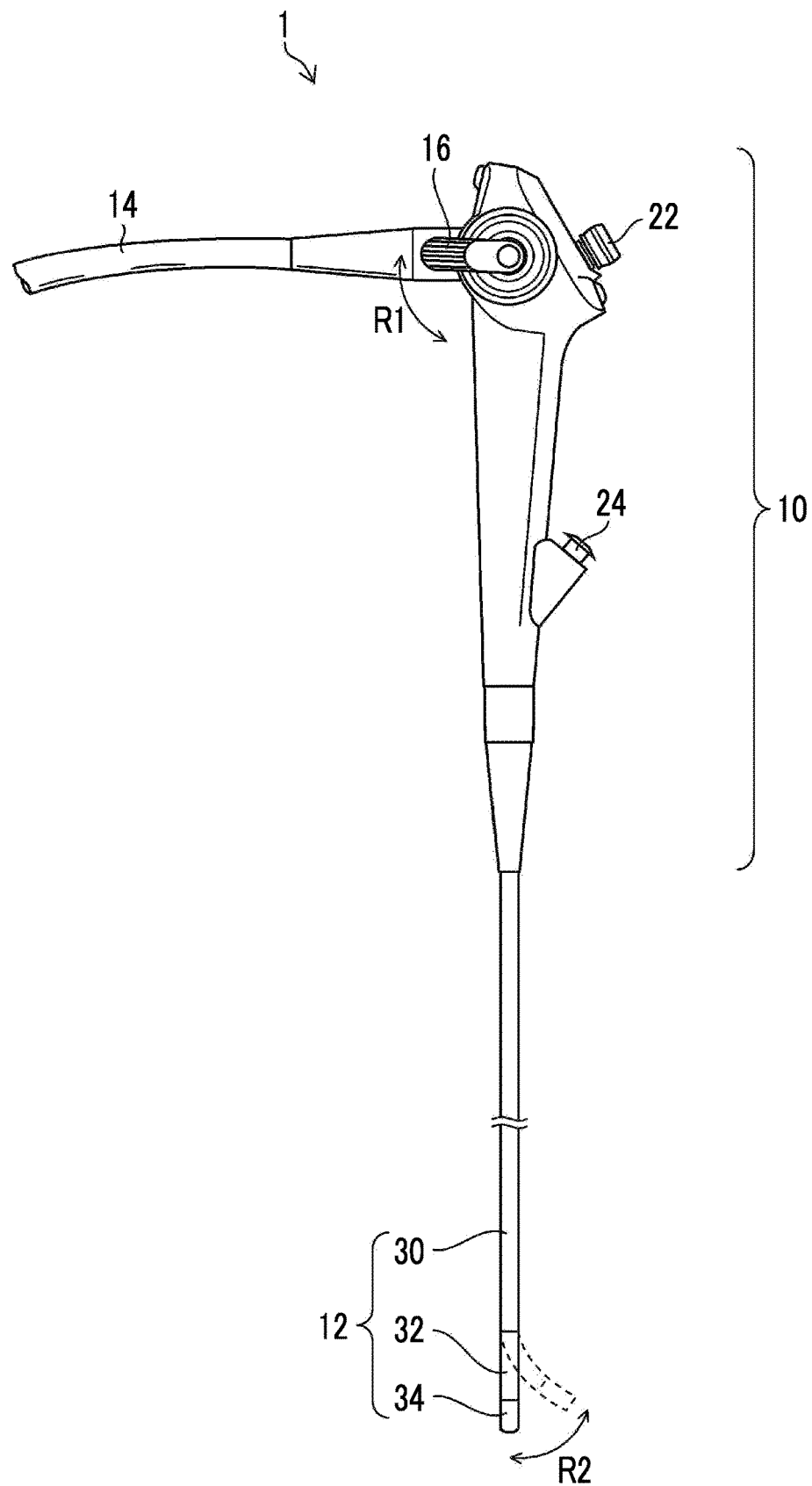
FIG. 1 is a general view of an ultrasonic endoscope.

FIG. 1 is a general view of the ultrasonic endoscope 1. As shown in FIG. 1, the ultrasonic endoscope 1 (hereinafter, simply abbreviated as an "endoscope 1") is configured with an operating part 10 that is gripped by a practitioner to perform various operations, an insertion part 12 that is inserted into a body cavity of a patient, and a universal cord 14. The endoscope 1 is connected to system constituent devices that configure an endoscope system, such as a processor device and a light source device (not shown), through the universal cord 14.

The operating part 10 is provided with various operation members that are operated by the practitioner. For example, an angle lever 16, a suction button 22, and the like are provided.

The operating part 10 is provided with a treatment tool inlet port 24 through which a treatment tool is inserted into a treatment tool insertion channel 23 (see FIG. 3) that is inserted into the insertion part 12.

The insertion part 12 extends from a distal end of the operating part 10 and is formed in a small-diameter elongated shape as a whole. The insertion part 12 is configured with, in order from a proximal end side toward a distal end side, a soft part 30, a bendable part 32, and a distal end hard part 34 as a distal end part.

The soft part 30 occupies most of the insertion part 12 from the proximal end side and has enough flexibility to be bent in any direction. In a case where the insertion part 12 is inserted into the body cavity, the soft part 30 is bent along an insertion path into the body cavity.

The bendable part 32 is bent in an up-down direction (R2 direction) by rotating the angle lever 16 of the operating part 10 in an R1 direction. With the bending operation of the bendable part 32, the distal end hard part 34 can be directed in a desired direction.

Though details will be described referring to FIGS. 2 and 3 described below, the distal end hard part 34 comprises an observation optical system 40 and illumination optical systems 44 that are provided to capture an observation image in the body cavity, an ultrasound transducer 50 that acquires an ultrasound image, and an outlet port 52 from which the treatment tool inserted from the treatment tool inlet port 24 is led out.

The universal cord 14 includes a signal cable 54, a signal cable 56, and a light guide 58 shown in FIG. 3 described below. A connector is provided in an end portion (not shown) of the universal cord 14. The connector is connected to predetermined system constituent devices that configure the endoscope system, such as a processor device and a light source device. As a result, power, control signals, illumination light, and the like necessary for the operation of the endoscope 1 are supplied from the system constituent devices to the endoscope 1. Conversely, data of the observation image acquired by the observation optical system 40 and data of the ultrasound image acquired by the ultrasound transducer 50 are transmitted from the endoscope 1 to the system constituent devices. The observation image and the ultrasound image transmitted to the system constituent devices are displayed on a monitor, and the practitioner or the like can observe the images.

The configuration of the operating part 10 is not limited to the aspect shown in FIG. 1. A pair of angle knobs may be provided instead of the angle lever 16, and the bendable part 32 may be bent in the up-down direction and in a right-left direction by rotating a pair of angle knobs. An air/water supply button may be provided in the operating part 10, and gas, such as air, a liquid for cleaning, and the like may be supplied to the distal end hard part 34 by operating the air/water supply button.

Configuration of Distal End Constituent Part

Figure 2:
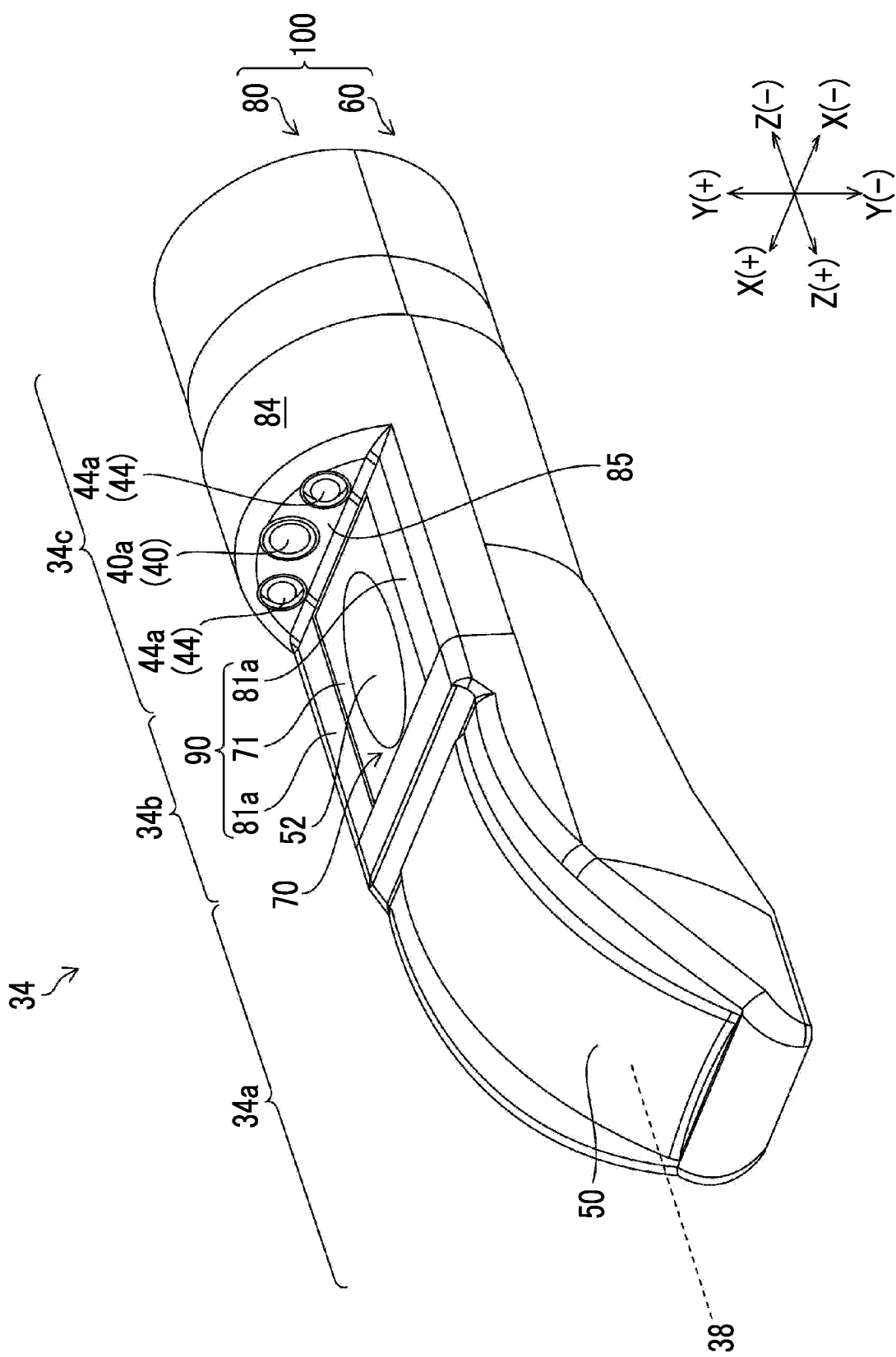
FIG. 2 is a perspective view of a distal end hard part.

FIG. 2 is a perspective view of the distal end hard part 34. FIG. 3 is an exploded perspective view of the distal end hard part 34.

A Z direction in the drawing is a direction parallel to a longitudinal axis 38 of the distal end hard part 34 (insertion part 12). A Z(+) direction side of the Z direction in the drawing is a distal end side of the distal end hard part 34, and a Z(−) direction side is a proximal end side of the distal end hard part 34. A Y direction in the drawing is a direction perpendicular to the Z direction and is an up-down direction in each drawing in the present embodiment. A Y(+) direction side as a one direction side of the Y direction is an up direction in the drawing, and a Y(−) direction side as the other direction side of the Y direction is a down direction in the drawing. An X direction in the drawing is a direction perpendicular to both the Z direction and the Y direction.

Figure 3:
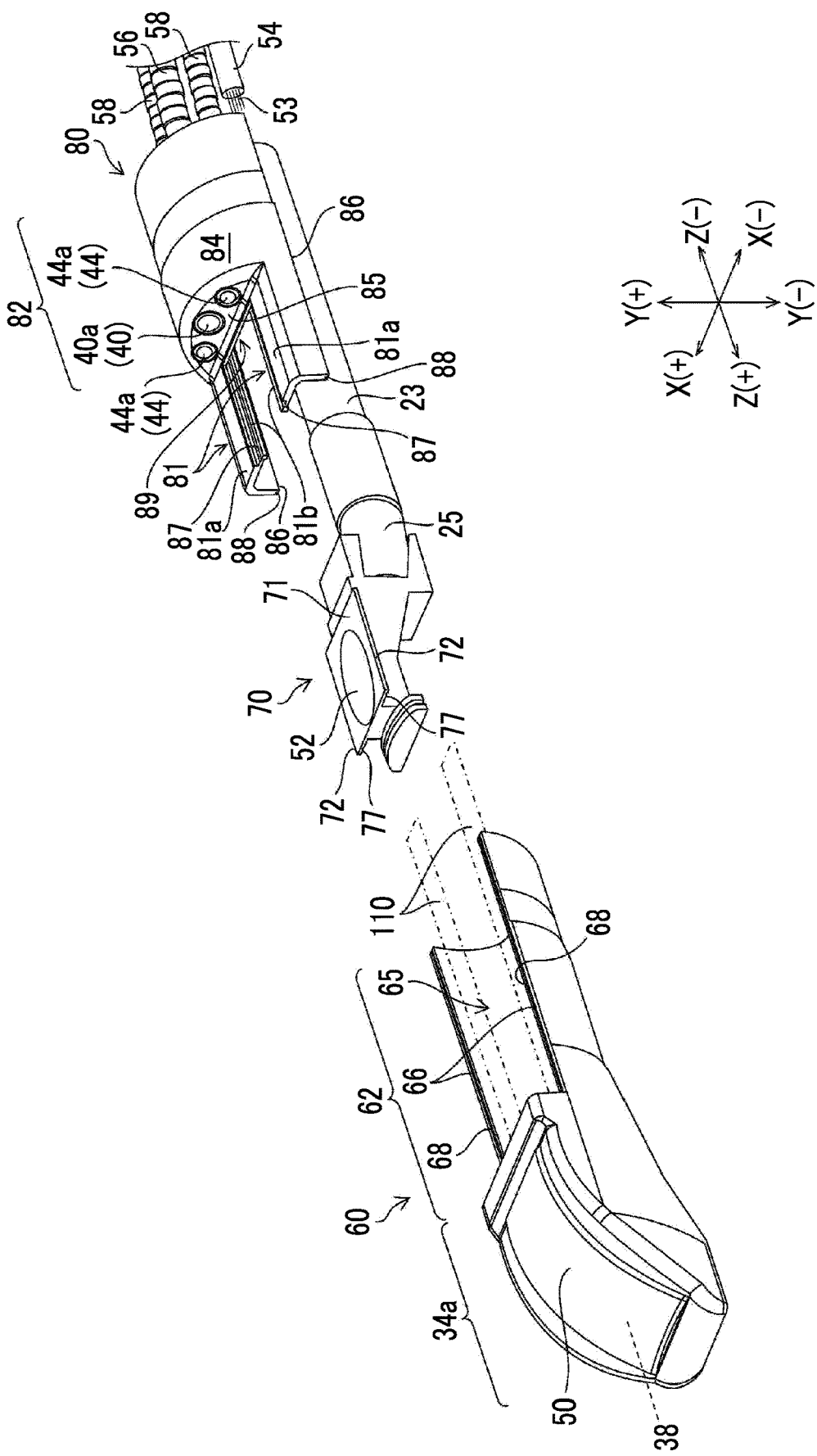
FIG. 3 is an exploded perspective view of the distal end hard part.

As shown in FIGS. 2 and 3, the distal end hard part 34 is configured by combining an ultrasound block component 60, a channel block component 70, and an optical system block component 80. The ultrasound block component 60 and the optical system block component 80 are components that configure a distal end body block component 100. The distal end hard part 34 comprises an ultrasonic attachment part 34a, an outlet port forming part 34b, and a body part 34c from the distal end side toward the proximal end side of the distal end hard part 34 in a state in which the respective block components are combined (see FIG. 2).

A forming material of the ultrasound block component 60 is an insulating material having insulation, and is formed of a resin material, for example, plastic, such as polysulphone and polyether imide. The ultrasound block component 60 comprises the ultrasonic attachment part 34a and an optical system block component attachment part 62 from a distal end side toward a proximal end side thereof. The ultrasonic attachment part 34a and the optical system block component attachment part 62 are formed integrally.

The ultrasound transducer 50 is attached to the ultrasonic attachment part 34a in a posture tilted forward (inclined) to the Y(−) direction side with respect to the longitudinal axis 38 as viewed from the X direction side. The ultrasound transducer 50 is a convex type that has an ultrasonic wave transmitting and receiving surface on which ultrasound oscillators that transmit and receive ultrasonic waves are arranged in a curved shape along a direction of the longitudinal axis 38. Data that generates an ultrasound image of a site to be observed is acquired by the ultrasound transducer 50. The number of ultrasound oscillators that configure the ultrasound transducer 50 is not limited.

The optical system block component attachment part 62 has a substantially semi-cylindrical shape corresponding to a divided part on the Y(−) direction side (a lower half side) out of two divided parts obtained by dividing the outlet port forming part 34b and the body part 34c into two parts in the Y direction (into two parts vertically). For this reason, the optical system block component attachment part 62 has an attachment part opening 65 that is opened on the Y(+) direction side.

The attachment part opening 65 is formed in parallel to an XZ plane and along the Z direction. Inside the attachment part opening 65 of the optical system block component attachment part 62, a flexible printed circuit part 110 that connects the ultrasound transducer 50 and the signal cable 54 is disposed. The system constituent device generates an ultrasound signal for making the ultrasound transducer 50 generate ultrasonic waves and supplies the ultrasound signal to the ultrasound transducer 50 through the signal cable 54 and the flexible printed circuit part 110. The configuration of the flexible printed circuit part 110 that is a feature of the present invention will be described below.

In the optical system block component attachment part 62, a pair of guide portions 66 that forms the attachment part opening 65 is formed, and the pair of guide portions 66 extends to the Z(−) direction side along the attachment part opening 65. The optical system block component 80 is attached to the pair of guide portions 66 while being slid in the Z direction. With this, the optical system block component 80 is attached to the ultrasound block component 60 through the pair of guide portions 66.

The pair of guide portions 66 is provided with sealing material filling groove portions 68 to secure airtightness of connection surfaces to the optical system block component 80. In a case where groove portions 88 are provided in a pair of guided portions 86 of the optical system block component 80 described below to be matching surface of the pair of guide portion 66, the groove portions 68 may not be provided in the pair of guide portions 66.

The channel block component 70 configures the outlet port forming part 34b along with the optical system block component 80, and a forming material of the channel block component 70 is metal. As metal, a known metal material can be used. The channel block component 70 has the outlet port 52 of the treatment tool that is opened on the Y(+) direction side, and a substantially rectangular opening forming surface 71 parallel to the XZ plane where the outlet port 52 is opened and along the Z direction (including the longitudinal axis 38, the same applies hereinafter).

At both end portions in the X direction of the opening forming surface 71 of the channel block component 70, a pair of flange surfaces 72 parallel to the XZ plane is formed along the Z direction (see FIG. 3). The pair of flange surfaces 72 is used for attachment of the channel block component 70 to the optical system block component 80, and extends outward (X direction) from both side surfaces in the X direction of the opening forming surface 71.

An in-block pipe line (not shown) is formed inside the channel block component 70. A distal end side of the in-block pipe line is connected to the outlet port 52, and a proximal end side of the in-block pipe line is connected to the treatment tool insertion channel 23 inserted into the insertion part 12, through a channel connection pipe 25. With this, a distal end of the treatment tool inserted from the treatment tool inlet port 24 is guided to the outlet port 52 by way of treatment tool insertion channel 23, the channel connection pipe 25, and the in-block pipe line, and is led out from the outlet port 52 to the outside.

The optical system block component 80 is formed of a resin material, like the ultrasound block component 60. The optical system block component 80 has a shape corresponding to a divided part on the Y(+) direction side (an upper half side) out of the two divided parts obtained by dividing the outlet port forming part 34b and the body part 34c into two parts in the Y direction (into two parts vertically).

The optical system block component 80 comprises, from a distal end side toward a proximal end side thereof, a pair of channel block component attachment portions 81 that is provided at an interval in the X direction, and an optical system storage portion 82 (see FIG. 3). The pair of channel block component attachment portions 81 and the optical system storage portion 82 are formed integrally.

A space for attaching the channel block component 70 is secured between the pair of channel block component attachment portions 81. In end portions on the Y(+) direction side of the pair of channel block component attachment portions 81, a pair of planes 81a having a shape parallel to the XZ plane and along the Z direction is formed. A pair of support surfaces 81b is formed at positions shifted from the pair of planes 81a in end portions to the above-described space side on the Y(−) direction side of the pair of channel block component attachment portions 81.

The pair of support surfaces 81b supports the pair of flange surfaces 72 from both sides in the X direction. With this, through the pair of flange surfaces 72 and the pair of support surfaces 81b, the channel block component 70 is slidably supported in the Z direction between the pair of channel block component attachment portions 81. Groove portions 77 and 87 for an adhesive to which an adhesive is applied are provided at positions facing the pair of flange surfaces 72 and the pair of support surfaces 81b.

In a case where the channel block component 70 is attached to the optical system block component 80, the opening forming surface 71 and the pair of planes 81a form a continuous plane 90. The continuous plane 90 is a plane parallel to the XZ plane and along the Z direction, and configures a part of an outer peripheral surface of the distal end hard part 34.

The optical system storage portion 82 has a semi-cylindrical shape, and has a convex surface 84 and a stepped surface 85. The convex surface 84 configures a part of the outer peripheral surface of the distal end hard part 34. In the optical system storage portion 82, a pair of guided portions 86 that extends in the Z(−) direction for forming a storage opening portion 89 opened in the Y(−) direction is formed. The pair of guided portions 86 is portions that are matching surfaces of the pair of guide portions 66 in assembling the distal end hard part 34.

The pair of guided portions 86 is provided with sealing material filling groove portions 88 to secure airtightness of connection surfaces to the ultrasound block component 60. In a case where the groove portions 68 are provided in the pair of guide portions 66, the groove portions 88 may not be provided.

The stepped surface 85 is provided with an observation window 40a of the observation optical system 40 and illumination windows 44a of a pair of illumination optical systems 44.

The observation optical system 40 includes an observation window 40a provided in the stepped surface 85, and a lens systems and a charge coupled device (CCD) type or a complementary metal oxide semiconductor (CMOS) type imaging element provided in the optical system storage portion 82. The imaging element (not shown) captures an observation image fetched from the observation window 40a through the lens system and outputs an imaging signal of the observation image to the system constituent devices through the signal cable 56 inserted into the insertion part 12.

The illumination optical systems 44 are provided on both sides (X(+) direction side and X(−) direction side) of the observation optical system 40, and include illumination windows 44a provided in the stepped surface 85, and a light guide 58 inserted into the insertion part 12. An emission end of the light guide 58 is disposed behind each illumination window 44a. The two illumination optical systems 44 are disposed on both sides of the observation optical system 40, and can secure an amount of light with no shadow of illumination.

In a case where the channel block component 70 is attached to the optical system block component 80, the pair of guided portions 86 is attached to the optical system block component attachment part 62 of the ultrasound block component 60 through the pair of guide portions 66.

As described above, the ultrasound block component 60, the channel block component 70, and the optical system block component 80 are combined, and the distal end hard part 34 is formed. With this, in a case where the distal end hard part 34 is viewed from the Y(+) direction side (upper side), the ultrasound transducer 50, the outlet port 52, and the stepped surface 85 (observation window 40a) are disposed in order from the distal end side toward the proximal end side of the distal end hard part 34.

In the distal end hard part 34, the outlet port 52 is disposed directly below (Y(−) direction side) the observation optical system 40, that is, the channel block component 70 is disposed at the center of X(+) and X(−), whereby the puncture needle or the treatment tool can be visually recognized by the observation optical system 40 from a moment of protruding from the outlet port 52, and safe treatment can be performed.

On the other hand, since the channel block component 70 is disposed at the center of the distal end hard part 34, it is important to efficiently store ultrasonic cables in the distal end hard part 34. Accordingly, the present inventors have conducted intensive studies and have completed a flexible printed circuit part of the present invention capable of performing efficient storage.

Configuration of Flexible Printed Circuit Part

Next, the configuration of the flexible printed circuit part 110 that is the feature of the present invention will be described.

Figure 4:
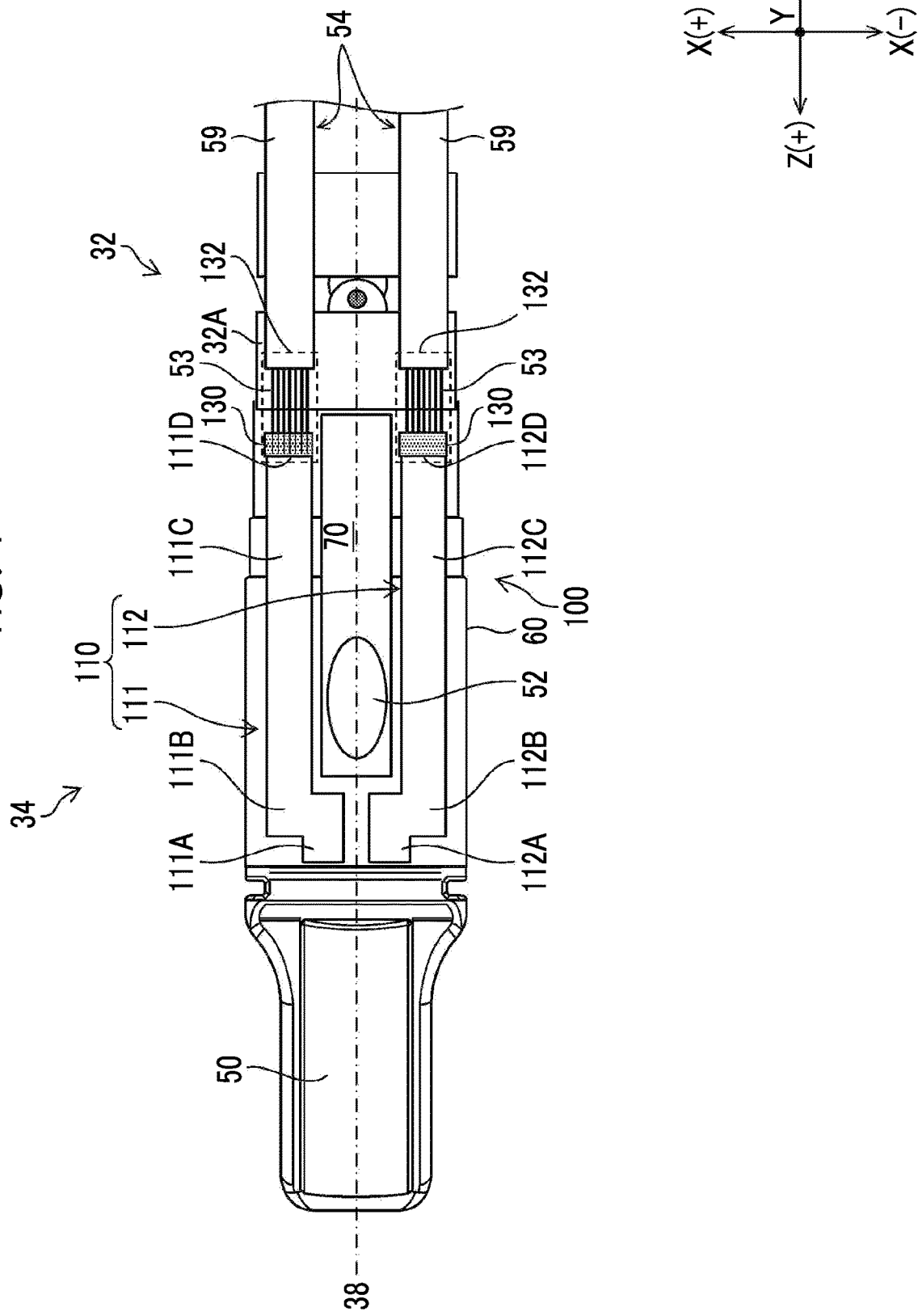
FIG. 4 is a plan view showing the internal structure of the distal end hard part including a flexible printed circuit part of the present embodiment.

FIG. 4 is a plan view showing the internal structure of the distal end hard part 34 including the flexible printed circuit part 110 of the present embodiment. In FIG. 4, to clearly describe the invention, portions not related to the description will be omitted. The same also applies to the drawings described below.

As shown in FIG. 4, inside the distal end hard part 34, the flexible printed circuit part 110 is disposed on a proximal end side (Z(−) direction side) of the ultrasound transducer 50. The flexible printed circuit part 110 of the present embodiment comprises two flexible printed circuits 111 and 112 (first flexible printed circuit 111 and second flexible printed circuit 112).

The flexible printed circuit part 110 is a flexible flat plate-shaped wiring board unit in which wiring portions for electrically connecting the ultrasound transducer 50 and the signal cable 54 are provided. A distal end (an end on the (Z(+) direction side) of each of the flexible printed circuits configuring the flexible printed circuit part 110 is connected to an electrode (not shown) of the ultrasound transducer 50. A proximal end (an end on the Z(−) direction side) of each of the flexible printed circuits 111 and 112 is connected to the signal cable 54. The signal cable 54 is a cable member that is inserted from the insertion part 12 to the universal cord 14 and that is provided to transmit and receive various signals between the above-described system constituent devices and the ultrasound transducer 50.

Here, the signal cable 54 is configured by bundling a plurality of cables 53 with an insulating outer coat 59, the outer coat 59 is removed on the distal end side (Z(+) direction side) thereof, and each cable 53 is exposed in a loose state. Each loose cable 53 is connected to the proximal end of each of the flexible printed circuits 111 and 112.

In the example shown in FIG. 4, each loose cable 53 exposed from the distal end side of the signal cable 54 is disposed in a region between a distal end bendable piece 32A disposed on a most distal end side (Z(+) direction side) among bendable pieces configuring the bendable part 32 and a proximal end portion (a portion on the proximal end side with respect to the outlet port 52) of the distal end hard part 34. Then, a bonding portion (corresponding to a first cable bonding portion 111D and a second cable bonding portion 112D described below) of each loose cable 53 and each of the flexible printed circuits 111 and 112 is positioned in the proximal end portion of the distal end hard part 34.

Hereinafter, the configuration of the flexible printed circuit part 110 of the present embodiment will be described in detail referring to FIG. 4.

As shown in FIG. 4, the first flexible printed circuit 111 and the second flexible printed circuit 112 that configure the flexible printed circuit part 110 are disposed inside the distal end hard part 34. The first flexible printed circuit 111 and the second flexible printed circuit 112 are provided in a linearly symmetrical shape with the longitudinal axis 38 interposed therebetween. The first flexible printed circuit 111 and the second flexible printed circuit 112 are formed in a crank shape (bent shape) bent in a direction away from each other at a position where the channel block component 70 incorporated inside the distal end body block component 100 is provided, from the distal end side (ultrasound transducer 50 side) toward the proximal end side (signal cable 54 side), and are provided on both sides of the channel block component 70 in a width direction (X direction). That is, the first flexible printed circuit 111 and the second flexible printed circuit 112 have a shape of preventing interference with the channel block component 70 in advance.

The first flexible printed circuit 111 and the second flexible printed circuit 112 have the crank shape bent in the direction away from each other as described above, whereby it is possible to easily secure a disposition space of the channel block component 70 that is disposed therebetween. With the use of the first flexible printed circuit 111 and the second flexible printed circuit 112 having the crank shape, it is possible to improve workability for electrically connecting the ultrasound transducer 50 and the signal cable 54.

In the present embodiment, the first flexible printed circuit 111 and the second flexible printed circuit 112 are not partially bent or torsionally deformed, and have a flat shape along a plane (XZ plane) parallel to the longitudinal axis 38 as shown in FIG. 4.

Here, the specific configuration of the first flexible printed circuit 111 and the second flexible printed circuit 112 will be described. As described above, since the first flexible printed circuit 111 and the second flexible printed circuit 112 have a linearly symmetrical shape with the longitudinal axis 38 interposed therebetween, and have a common basic shape, the configuration of the first flexible printed circuit 111 will be primarily described as a representative.

As shown in FIG. 4, the first flexible printed circuit 111 comprises a first transducer connection portion 111A, a first intermediate connection portion 111B, and a first offset wiring portion 111C.

The first transducer connection portion 111A is an example of a transducer connection portion (first transducer connection portion) of the present invention, and is a portion that configures a distal end side (a side on which the ultrasound transducer 50 is disposed) of the first flexible printed circuit 111. The first transducer connection portion 111A is electrically connected to the electrode (not shown) of the ultrasound transducer 50. The first transducer connection portion 111A is disposed at a position close to the longitudinal axis 38 compared to the first offset wiring portion 111C described below.

The first offset wiring portion 111C is an example of an offset wiring portion (first offset wiring portion) of the present invention, and is a portion that configures a proximal end side (a side on which the signal cable 54 is disposed) of the first flexible printed circuit 111. The first offset wiring portion 111C is disposed in an offset manner at a position away from the longitudinal axis 38 in the X(+) direction (a direction toward an outside in a radial direction of the longitudinal axis 38) with respect to the first transducer connection portion 111A. Then, the first offset wiring portion 111C is formed to extend along the channel block component 70 at a position adjacent to the channel block component 70.

The first intermediate connection portion 111B is an example of an intermediate connection portion (first intermediate connection portion) of the present invention, and is a portion that configures a connecting portion for connecting the first transducer connection portion 111A and the first offset wiring portion 111C. In the example shown in FIG. 4, although the first intermediate connection portion 111B is formed to extend in a direction (X(+) direction) perpendicular to the longitudinal axis 38, the present invention is not limited thereto, and the first intermediate connection portion 111B may be formed to be inclined with respect to the longitudinal axis 38. The same also applies to the second intermediate connection portion 112B described below.

The first offset wiring portion 111C has a first cable bonding portion 111D on a proximal end side (an opposite side to the first intermediate connection portion 111B). The first cable bonding portion 111D is an example of a cable bonding portion of the present invention, and is a portion to which the loose cables 53 are bonded. The first cable bonding portion 111D is positioned inside the distal end body block component 100. The loose cables 53 are bonded to the first cable bonding portion 111D, whereby the first flexible printed circuit 111 and the cables 53 are electrically bonded. The cables 53 and the first cable bonding portion 111D are electrically connected by, for example, solder or a conductive adhesive. The first cable bonding portion 111D is provided with an insulating member 130 to cover bonded portions of the cables 53.

The insulating member 130 is an example of an insulating member of the present invention, and is applied to the bonded portions of the cables 53 in the first cable bonding portion 111D by potting or the like. The insulating member 130 is not particularly limited as long as a resin material capable of securing insulation performance of the metallic channel block component 70, and the first flexible printed circuit 111 and the second flexible printed circuit 112 is used, and for example, silicon-based resin, acrylic resin, epoxy-based resin, polyimide-based resin, urethane-based resin, or the like can be appropriately used. As shown in a quadrangular frame of a broken line in FIG. 4, a coating member 132 that is externally fitted on the loose cables 53 exposed from the outer coat 59 and the insulating member 130 may be provided. In this case, it is possible to improve insulation performance with the coating member 132. The coating member 132 is, for example, a heat-shrinkable tube.

While the second flexible printed circuit 112 has a linearly symmetrical shape to the first flexible printed circuit 111 with the longitudinal axis 38 interposed therebetween, and is disposed to be separated from the first flexible printed circuit 111, the second flexible printed circuit 112 has the same basic configuration as the first flexible printed circuit 111.

That is, the second flexible printed circuit 112 is common to the first flexible printed circuit 111 in that a second transducer connection portion 112A, a second intermediate connection portion 112B, and a second offset wiring portion 112C are provided, and the second offset wiring portion 112C has a second cable bonding portion 112D (including an insulating member 130). The second transducer connection portion 112A, the second intermediate connection portion 112B, the second offset wiring portion 112C, and the second cable bonding portion 112D are examples of a transducer connection portion (second transducer connection portion), an intermediate connection portion (second intermediate connection portion), an offset wiring portion (second offset wiring portion), and a cable bonding portion of the present invention, respectively.

The second flexible printed circuit 112 is different from the first flexible printed circuit 111 as follows. That is, the second flexible printed circuit 112 is different from the first flexible printed circuit 111 in that, in the second flexible printed circuit 112, the second offset wiring portion 112C is disposed in an offset manner on an opposite side (X(−) direction side) to the first offset wiring portion 111C in the first flexible printed circuit 111 with the longitudinal axis 38 interposed therebetween. The second flexible printed circuit 112 is different from the first flexible printed circuit 111 in that the second intermediate connection portion 112B extends in an opposite direction to the first offset wiring portion 111C in the first flexible printed circuit 111.

With the flexible printed circuit part 110 (the first flexible printed circuit 111 and the second flexible printed circuit 112) of the present embodiment configured as above can obtain the following effects.

According to the present embodiment, the first flexible printed circuit 111 and the second flexible printed circuit 112 that configure the flexible printed circuit part 110 are formed in the crank shape in directions away from each other from the longitudinal axis 38. That is, the first flexible printed circuit 111 and the second flexible printed circuit 112 have a distance between the first offset wiring portion 111C and the second offset wiring portion 112C greater than a distance between the first transducer connection portion 111A and the second transducer connection portion 112A. For this reason, in performing work for electrically connecting the ultrasound transducer 50 and the signal cable 54, the ultrasound transducer 50 and the signal cable 54 are connected using the first flexible printed circuit 111 and the second flexible printed circuit 112, whereby it is possible to easily avoid interference with the channel block component 70 and to improve efficiency of work without requiring a lot of labor for styling the cables.

According to the present embodiment, the first cable bonding portion 111D and the second cable bonding portion 112D positioned on the proximal end side of the first flexible printed circuit 111 and the proximal end side of the second flexible printed circuit 112, respectively, are positioned inside the distal end body block component 100, and the bonded portions of the loose cables 53 are covered with the insulating member 130. For this reason, even in a case where the bendable part 32 repeats the bending operation, since the first cable bonding portion 111D and the second cable bonding portion 112D are structured to be less susceptible to the bending operation, it is possible to suppress disconnection from the cables 53 and to secure insulation performance of the metallic channel block component 70, and the first flexible printed circuit 111 and the second flexible printed circuit 112.

Therefore, according to the present embodiment, a configuration is employed in which the ultrasound transducer 50 and the signal cable 54 are electrically connected using the flexible printed circuit part 110 (first flexible printed circuit 111 and second flexible printed circuit 112), whereby, even in the distal end hard part 34 with a diameter reduced (distal end body block component 100), it is possible to easily perform insertion into the flexible printed circuit part 110 while avoiding interference with the component (channel block component 70) disposed inside thereof. As a result, it is possible to improve manufacturing suitability.

In the present embodiment, although an aspect where the first flexible printed circuit 111 and the second flexible printed circuit 112 that configure the flexible printed circuit part 110 have the linearly symmetrical shape with the longitudinal axis 38 interposed therebetween has been shown as a preferred aspect, the flexible printed circuit may have at least the crank shape described above and may not necessarily have the linearly symmetrical shape. The first flexible printed circuit 111 and the second flexible printed circuit 112 may have a linearly symmetrical shape with a straight line (for example, a straight line parallel to the longitudinal axis 38) different from the longitudinal axis 38.

In the present embodiment, although an aspect where the flexible printed circuit part 110 is configured with the first flexible printed circuit 111 and the second flexible printed circuit 112 has been shown as a preferred aspect, the present invention is not limited thereto, and the flexible printed circuit part 110 may be configured only with any one flexible printed circuit of the first flexible printed circuit 111 or the second flexible printed circuit 112.

MODIFICATION EXAMPLES

Hereinafter, modification examples of the present embodiment will be described.

First Modification Example

Figure 5:
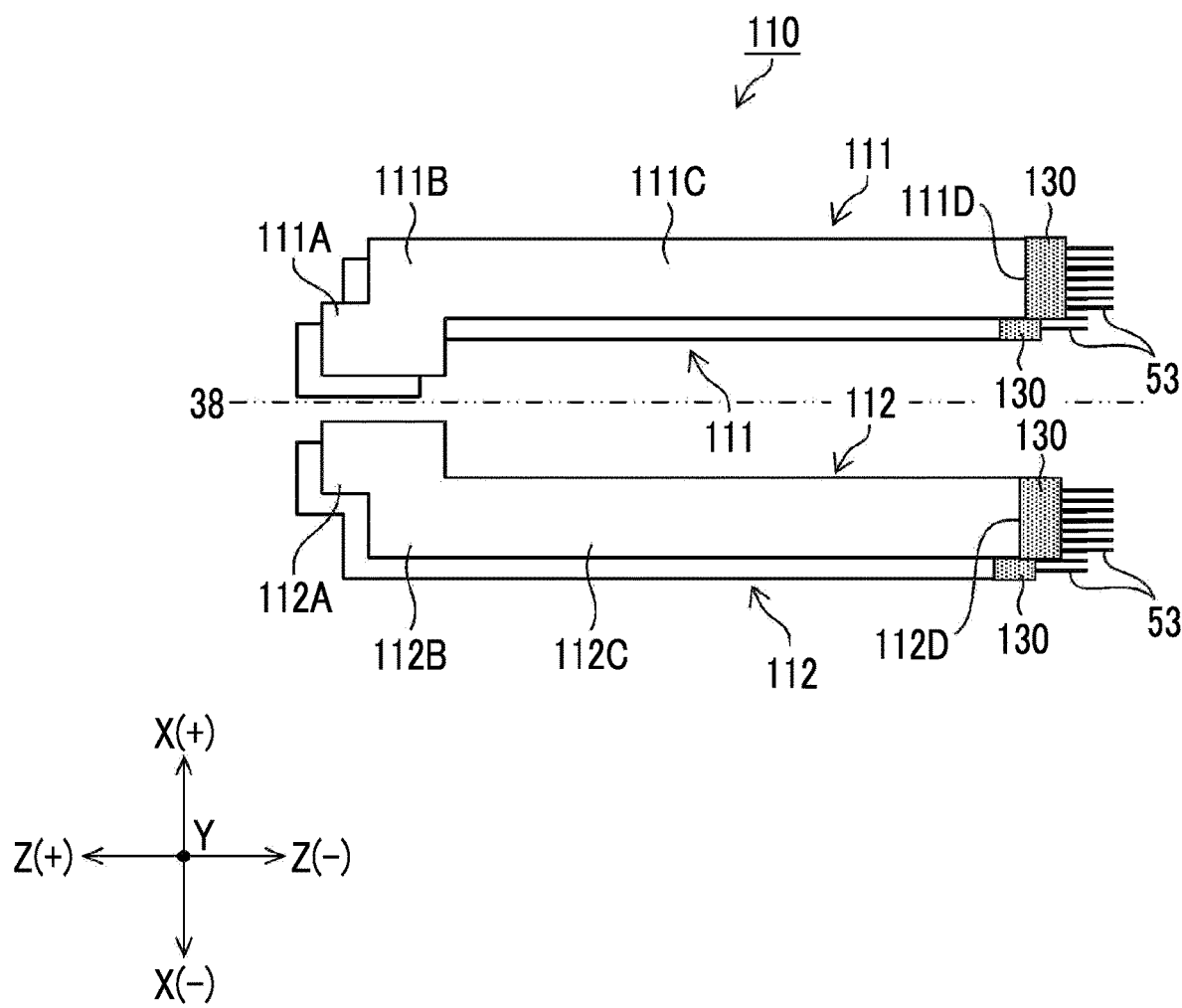
FIG. 5 is a diagram illustrating a first modification example.

FIG. 5 is a diagram illustrating a first modification example. In FIG. 5, portions common to the present embodiment described above are represented by the same reference numerals, and description thereof will not be repeated.

In the first modification example shown in FIG. 5, a plurality of first flexible printed circuit 111 and second flexible printed circuit 112 that configure the flexible printed circuit part 110 in the present embodiment are disposed to overlap each other in a thickness direction (Y direction) thereof. In FIG. 5, although an example where two flexible printed circuit parts 110 are disposed to overlap each other is shown, three or more flexible printed circuit parts may be disposed to overlap each other. As shown in FIG. 4, since the first flexible printed circuit 111 and the second flexible printed circuit 112 are limited in a width direction (X direction) to avoid interference with the channel block component 70, a plurality of flexible printed circuit parts 110 are disposed to overlap each other in the thickness direction (Y direction) thereof, whereby it is possible to easily cope with multi-channel of the ultrasound transducer 50. Since it is possible to suppress an increase in width of each flexible printed circuit part 110, it is possible to effectively utilize a limited space inside the distal end hard part 34 and to achieve a reduction in diameter of the distal end hard part 34.

Second Modification Example

FIG. 6 is a diagram illustrating a second modification example. In FIG. 6, portions common to the present embodi- In the second modification example shown in FIG. 6, the first flexible printed circuit 111 and the second flexible printed circuit 112 that configure the flexible printed circuit part 110 in the first modification example described above are disposed to be shifted in a direction approaching the longitudinal axis 38. That is, as viewed with the configuration shown in the first modification example as a reference, a plurality of (in the present example, two) first flexible printed circuits 111 that overlap in the thickness direction (Y direction) are disposed to be shifted in the X(−) direction, and a plurality of (in the present example, two) second flexible printed circuits 112 that overlap in the thickness direction (Y direction) are disposed to be shifted in the X(+) direction. Then, the first transducer connection portion 111A of each first flexible printed circuit 111 and the second transducer connection portion 112A of each second flexible printed circuit 112 are disposed to alternately overlap each other in the thickness direction (Y direction). In the second modification example, while the disposition space of the component (channel block component 70) that is disposed between the first offset wiring portion 111C and the second offset wiring portion 112C is narrowed compared to the first modification example, it is possible to reduce maximum widths (maximum widths in the X direction) of each of the first flexible printed circuits 111 and the second flexible printed circuits 112 compared to the first modification example and to achieve a reduction in diameter of the distal end hard part 34.

Third Modification Example

FIG. 7 is a diagram illustrating a third modification example. In FIG. 7, portions common to the present embodiment described above are represented by the same reference numerals, and description thereof will not be repeated.

In the present embodiment, as described above, the first flexible printed circuit 111 and the second flexible printed circuit 112 that configure the flexible printed circuit part 110 are not partially bent or torsionally deformed, and have a flat shape along the plane (XZ plane) parallel to the longitudinal axis 38 as shown in FIG. 4. That is, in the first flexible printed circuit 111 of the present embodiment, plane directions of the first transducer connection portion 111A and the first offset wiring portion 111C are the same direction. The same also applies to the second flexible printed circuit 112.

In contrast, in the third modification example, the first flexible printed circuit 111 and the second flexible printed circuit 112 are partially bent or torsionally deformed, and plane directions of the first offset wiring portion 111C and the second offset wiring portion 112C are directed in directions different from the present embodiment.

Specifically, as shown in FIG. 7, the first flexible printed circuit 111 is bent or torsionally deformed along a straight line parallel to the longitudinal axis 38 in a boundary portion of the first intermediate connection portion 111B and the first offset wiring portion 111C, and the plane direction (YZ plane) of the first offset wiring portion 111C is a direction perpendicular to the plane directions (XZ plane directions) of the first transducer connection portion 111A and the first intermediate connection portion 111B.

The same also applies to the second flexible printed circuit 112. The second flexible printed circuit 112 is bent or torsionally deformed along a straight line parallel to the longitudinal axis 38 in a boundary portion of the second intermediate connection portion 112B and the second offset wiring portion 112C, and a plane direction (YZ plane) of the second offset wiring portion 112C is a direction perpendicular to plane directions (XZ plane directions) of the second transducer connection portion 112A and the second intermediate connection portion 112B.

In other words, the plane directions of the first offset wiring portion 111C and the second offset wiring portion 112C are perpendicular to a plane direction (XZ plane direction) of the opening forming surface 71 (see FIG. 2) in which the outlet port 52 of the treatment tool is formed.

In the first flexible printed circuit 111 and the second flexible printed circuit 112, the bent or torsionally deformed portions are not limited to the boundary portions, and may be, for example, middle portions in an extension direction of the first intermediate connection portion 111B and the second intermediate connection portion 112B.

In this way, according to the third modification example, the first flexible printed circuit 111 and the second flexible printed circuit 112 are partially bent or torsionally deformed, and the plane directions of the first offset wiring portion 111C and the second offset wiring portion 112C are disposed in directions perpendicular to (including substantially perpendicular to) the plane directions of at least the first transducer connection portion 111A and the second transducer connection portion 112A (that is, the plane direction of the opening forming surface 71). With this, it is possible to secure a wide disposition space of the component (channel block component 70) that is disposed between the first offset wiring portion 111C and the second offset wiring portion 112C. It is possible to reduce the maximum widths (the maximum widths in the X direction) of the first flexible printed circuit 111 and the second flexible printed circuit 112 and to achieve a reduction in diameter of the distal end hard part 34.

Fourth Modification Example

Figure 8:
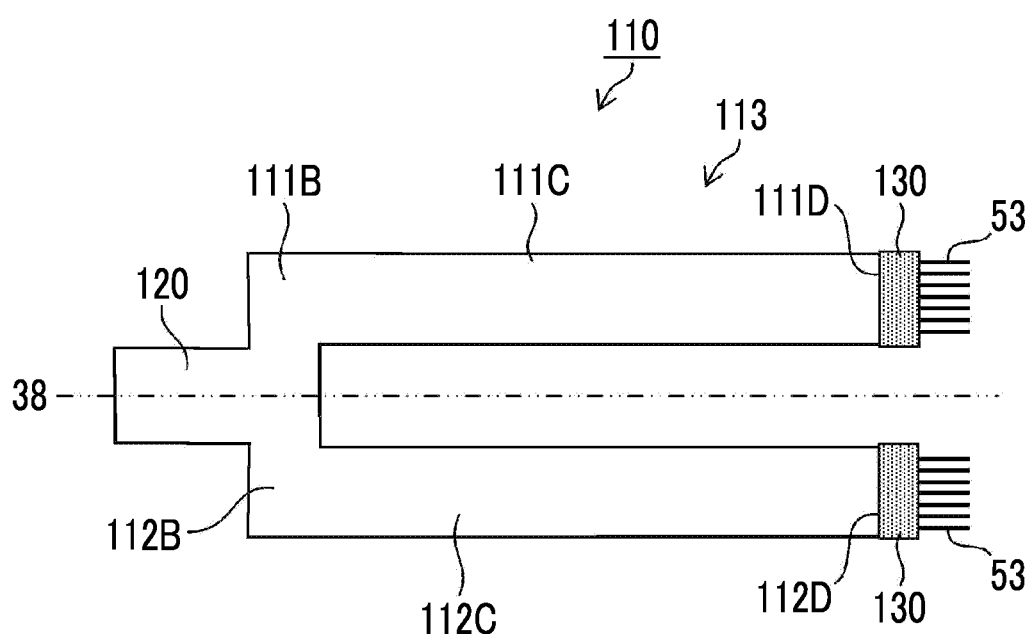
FIG. 8 is a diagram illustrating a fourth modification example.

FIG. 8 is a diagram illustrating a fourth modification example. In FIG. 8, portions common to the present embodiment described above are represented by the same reference numerals, and description thereof will not be repeated.

In the present embodiment, while the flexible printed circuit part 110 is configured with the two flexible printed circuits 111 and 112 (first flexible printed circuit 111 and second flexible printed circuit 112), in the fourth modification example, the flexible printed circuit part 110 is configured with one flexible printed circuit 113. The flexible printed circuit 113 that configures the flexible printed circuit part 110 in the fourth modification example corresponds to a flexible printed circuit in which the first transducer connection portion 111A of the first flexible printed circuit 111 and the second transducer connection portion 112A of the second flexible printed circuit 112 in the present embodiment are substituted with one common transducer connection portion 120.

That is, the flexible printed circuit 113 in the fourth modification example comprise the common transducer connection portion 120 disposed on a distal end side (ultrasound transducer 50 side). The flexible printed circuit 113 comprises a first intermediate connection portion 111B and a second intermediate connection portion 112B are connected to a proximal end side of the common transducer connection portion 120 to branch off in directions away from each other, the first offset wiring portion 111C is connected to the first intermediate connection portion 111B, and the second offset wiring portion 112C is connected to the second intermediate connection portion 112B. The configurations of the first cable bonding portion 111D and the second cable bonding portion 112D (including the insulating member 130) that are provided on the proximal end side of the first offset wiring portion 111C and the proximal end side of the second offset wiring portion 112C, respectively, are the same as in the present embodiment.

In the fourth modification example, as in the present embodiment described above, even in the distal end hard part 34 with a diameter reduced (distal end body block component 100), it is possible to easily perform insertion into the flexible printed circuit part 110 while avoiding interference with the component (channel block component 70) that is disposed inside thereof. As a result, it is possible to improve manufacturing suitability.

Fifth Modification Example

Figure 9:
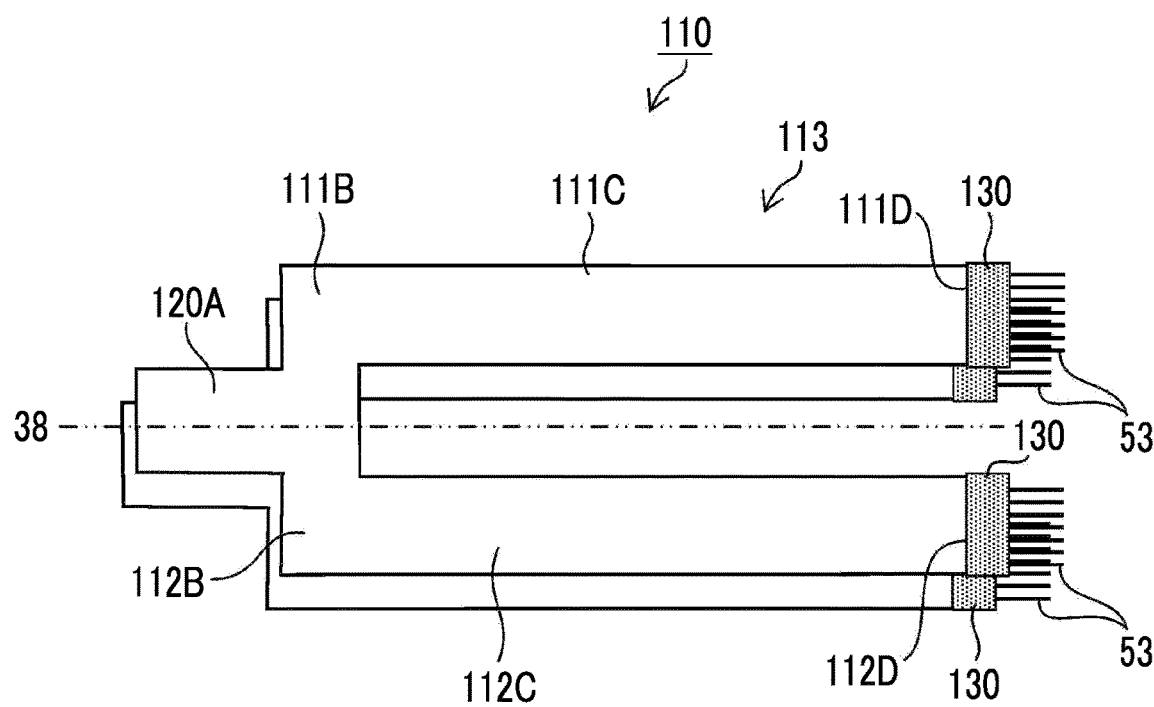
FIG. 9 is a diagram illustrating a fifth modification example.

FIG. 9 is a diagram illustrating a fifth modification example. In FIG. 9, portions common to the present embodiment described above are represented by the same reference numerals, and description thereof will not be repeated.

In the fifth modification example shown in FIG. 9, as in the first modification example described above, a plurality of (in the present example, two) flexible printed circuits 113 that configure the flexible printed circuit part 110 in the fourth modification example are disposed to overlap each other in the thickness direction (Y direction) thereof. With this, it is possible to easily cope with multi-channel of the ultrasound transducer 50. Since it is possible to suppress an increase in width of the flexible printed circuit part 110 (flexible printed circuit 113), it is possible to effectively utilize a limited space inside the distal end hard part 34 and to achieve a reduction in diameter of the distal end hard part 34.

Sixth Modification Example

FIG. 10 is a diagram illustrating a sixth modification example. In FIG. 10, portions common to the present embodiment described above are represented by the same reference numerals, and description thereof will not be repeated. In FIG. 10, only the first flexible printed circuit 111 is shown as a representative of the first flexible printed circuit 111 and the second flexible printed circuit 112 that configure the flexible printed circuit part 110.

As shown in 10A and 10B of FIG. 10, as in the present embodiment, the first flexible printed circuit 111 of the sixth modification example comprises the first transducer connection portion 111A, the first intermediate connection portion 111B, and the first offset wiring portion 111C, the first offset wiring portion 111C has the first cable bonding portion 111D to which the loose cables 53 are bonded, and the first cable bonding portion 111D is covered with the insulating member 130; however, the sixth modification example is different from the present embodiment in that the first offset wiring portion 111C is disposed inside the distal end hard part 34 (distal end body block component 100) in a state of being in a cylindrical shape (see 10A of FIG. 10) or a tubular shape (10B of FIG. 10). The first offset wiring portion 111C may be in a cylindrical shape or a tubular shape partially, not wholly. The same also applies to the second flexible printed circuit 112.

According to the sixth modification example, compared to the present embodiment where the first flexible printed circuit 111 and the second flexible printed circuit 112 that configure the flexible printed circuit part 110 are disposed in a flat state, a degree of freedom of disposition of the flexible printed circuit part 110 increases, it is possible to further save a space, and insertion inside the small-diameter distal end body block component 100 is facilitated. The present modification example can also be applied to the flexible printed circuit 113 in the fourth modification example and the fifth modification example described above.

Another Invention

Figure 11:
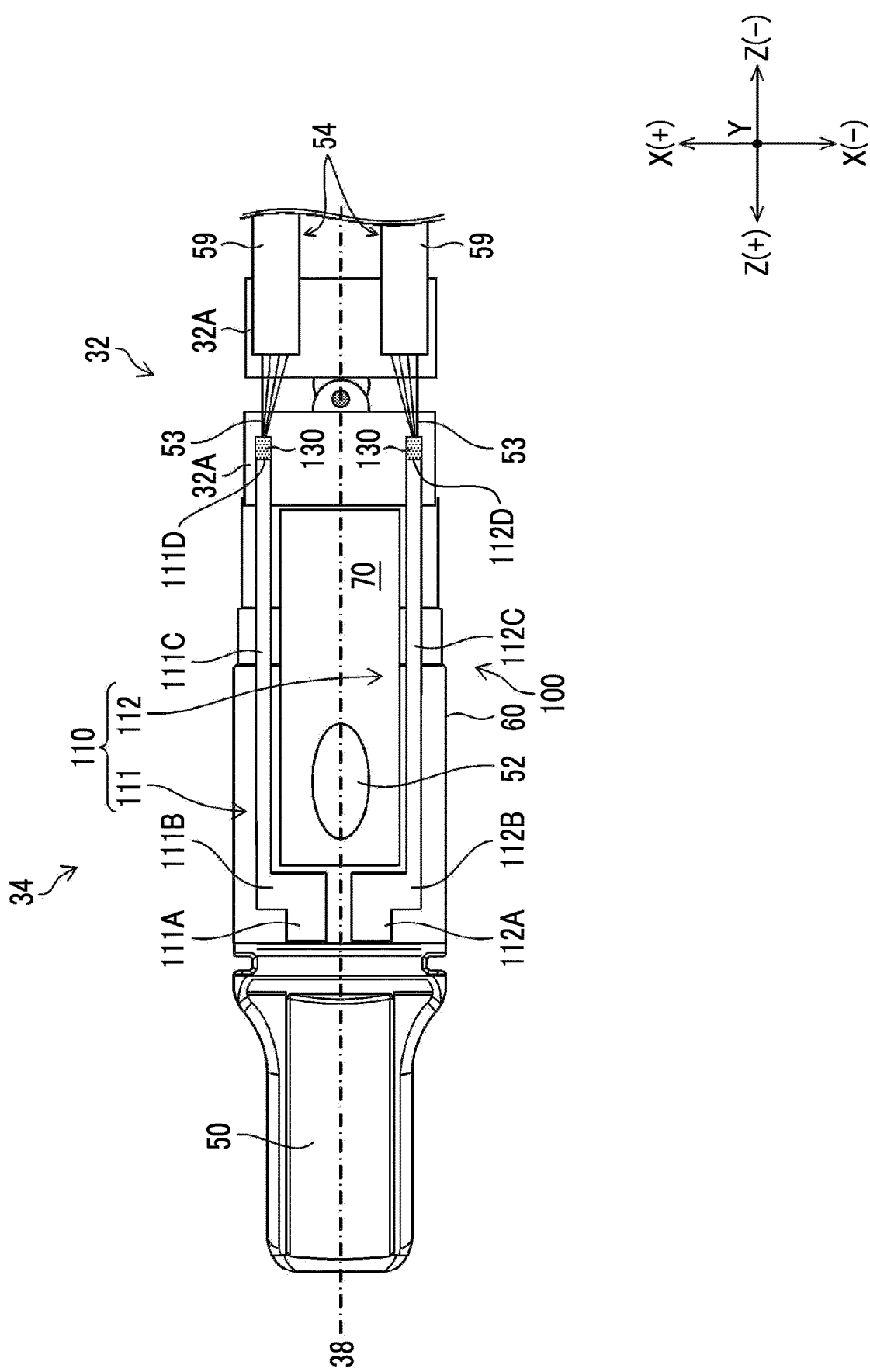
FIG. 11 is an explanatory view illustrating another invention.

FIG. 11 is an explanatory view illustrating another invention.

In the embodiment and each modification example described above, although a configuration is made in which the first cable bonding portion 111D and the second cable bonding portion 112D are positioned inside the distal end body block component 100, and the bonded portion of the loose cables 53 is covered with the insulating member 130, as shown in FIG. 11, the first cable bonding portion 111D and the second cable bonding portion 112D (including the insulating member 130) may be disposed inside the distal end bendable piece 32A positioned on the most distal end side among the bendable pieces configuring the bendable part 32. The distal end bendable piece 32A is a component that is fixed to the distal end body block component 100, and is less susceptible to the bending operation of the bendable part 32 compared to other bendable pieces disposed on the proximal end side with respect to the distal end bendable piece 32A even in a case where the bending operation of the bendable part 32 is performed. For this reason, in the present configuration, it is possible to suppress disconnection of the first cable bonding portion 111D and the second cable bonding portion 112D, and the cables 53.

In the example shown in FIG. 11, as in the third modification example (see FIG. 7), although the first flexible printed circuit 111 and the second flexible printed circuit 112 that configure the flexible printed circuit part 110 are partially bent or torsionally deformed, the present invention is not limited thereto, and for example, as in the present embodiment (see FIG. 4), the first flexible printed circuit 111 and the second flexible printed circuit 112 may be in a flat shape along the plane (XZ plane) parallel to the longitudinal axis 38.

EXPLANATION OF REFERENCES

1: ultrasonic endoscope
10: operating part
12: insertion part
14: universal cord
16: angle lever
22: suction button
23: treatment tool insertion channel
24: treatment tool inlet port
25: channel connection pipe
30: soft part
32: bendable part
32A: distal end bendable piece
34: distal end hard part
34a: ultrasonic attachment part
34b: outlet port forming part
34c: body part
38: longitudinal axis
40: observation optical system
40a: observation window
44: illumination optical system
44a: illumination window
50: ultrasound transducer
52: outlet port
53: cable 54: signal cable
56: signal cable
58: light guide
59: outer coat
60: ultrasound block component
62: optical system block component attachment part
65: attachment part opening
66: guide portion
68: groove portion
70: channel block component
71: opening forming surface
72: flange surface
77: groove portion for adhesive
80: optical system block component
81: channel block component attachment portion
81a: plane
81b: support surface
82: optical system storage portion
84: convex surface
85: stepped surface
86: guided portion
87: groove portion for adhesive
88: groove portion
89: storage opening portion
90: continuous plane
100: distal end body block component
110: flexible printed circuit part
111: first flexible printed circuit
111A: first transducer connection portion
111B: first intermediate connection portion
111C: first offset wiring portion
111D: first cable bonding portion
112: second flexible printed circuit
112A: second transducer connection portion
112B: second intermediate connection portion
112C: second offset wiring portion
112D: second cable bonding portion
113: flexible printed circuit
130: insulating member

What is claimed is:

1. An ultrasonic endoscope comprising:
an ultrasound transducer in a distal end part having a longitudinal axis;
a distal end body block component in which the ultrasound transducer, an observation optical system, and an illumination optical system are mounted;
a channel block component which is formed separately from the distal end body block component and in which a channel into which a treatment tool is inserted is mounted; and
a flexible printed circuit part that is disposed inside the distal end body block component and is connected to the ultrasound transducer,
wherein the flexible printed circuit part includes a transducer connection portion that is positioned on one side to be an ultrasound transducer side, an offset wiring portion that is positioned on the other side to be an opposite side to the one side, is disposed in an offset manner at a position away from the longitudinal axis toward an outside in a radial direction of the longitudinal axis with respect to the transducer connection portion and in a width direction of the flexible printed circuit part, and is formed along the channel block component, and an intermediate connection portion that connects the transducer connection portion and the offset wiring portion,
the offset wiring portion has a cable bonding portion to which loose cables are bonded, on an opposite side to the intermediate connection portion,
the cable bonding portion is covered with an insulating member, and
the insulating member is positioned inside the distal end body block component.

2. The ultrasonic endoscope according to claim 1,
wherein the flexible printed circuit part has a first offset wiring portion and a second offset wiring portion disposed in an offset manner in opposite directions to each other from the longitudinal axis, as the offset wiring portion, and
the channel block component is disposed between the first offset wiring portion and the second offset wiring portion.

3. The ultrasonic endoscope according to claim 2,
wherein the flexible printed circuit part has a first intermediate connection portion and a second intermediate connection portion extending in opposite directions to each other from the transducer connection portion toward the outside in the radial direction, as the intermediate connection portion,
the first intermediate connection portion and the first offset wiring portion are connected, and
the second intermediate connection portion and the second offset wiring portion are connected.

4. The ultrasonic endoscope according to claim 3,
wherein the flexible printed circuit part has a first transducer connection portion and a second transducer connection portion disposed separately from each other, as the transducer connection portion,
the first transducer connection portion and the first intermediate connection portion are connected, and
the second transducer connection portion and the second intermediate connection portion are connected.

5. The ultrasonic endoscope according to claim 1,
wherein the flexible printed circuit part has a first flexible printed circuit and a second flexible printed circuit disposed separately from each other.

6. The ultrasonic endoscope according to claim 1,
wherein a plurality of the flexible printed circuit parts are disposed to overlap in a thickness direction of the flexible printed circuit part.

7. The ultrasonic endoscope according to claim 1,
wherein a plane direction of the offset wiring portion is the same direction as a plane direction of the transducer connection portion.

8. The ultrasonic endoscope according to claim 1,
wherein the flexible printed circuit part is bent or torsionally deformed along a straight line parallel to the longitudinal axis, and
a plane direction of the offset wiring portion is a direction perpendicular to a plane direction of the transducer connection portion.

9. The ultrasonic endoscope according to claim 8,
wherein the channel block component has an opening forming surface in which an outlet port of the treatment tool is formed, and
the plane direction of the offset wiring portion is a direction perpendicular to a plane direction of the opening forming surface.

10. The ultrasonic endoscope according to claim 1,
wherein the flexible printed circuit part is disposed inside the distal end body block component in a state in which a shape of at least a part of the flexible printed circuit part is a cylindrical shape or a tubular shape.

11. The ultrasonic endoscope according to claim 1,
wherein the distal end body block component has an ultrasound block component in which the ultrasound transducer is mounted, and an optical system block component in which the observation optical system and the illumination optical system are mounted.

12. The ultrasonic endoscope according to claim 1,
wherein a forming material of the distal end body block component includes resin and metal, and
a forming material of the channel block component is metal.

13. The ultrasonic endoscope according to claim 1,
wherein the channel block component has an outlet port for the treatment tool,
the flexible printed circuit part extends to the proximal end side than the outlet port for the treatment tool in a direction of the longitudinal axis, and
the offset wiring portion is bonded to a loose cable on the proximal end side than the outlet port for the treatment tool.

* * * * *